US008614061B2

(12) United States Patent
Brabetz et al.

(10) Patent No.: US 8,614,061 B2
(45) Date of Patent: Dec. 24, 2013

(54) COMBINATION OF FLUORESCENT DYES FOR THE DETECTION OF NUCLEIC ACIDS

(75) Inventors: Werner Brabetz, Dresden (DE); Cornelia Weber, Grosserkmannsdorf (DE)

(73) Assignee: Qiagen, GmbH, Hilden (DE)

( * ) Notice: Subject to any disclaimer, the term of this patent is extended or adjusted under 35 U.S.C. 154(b) by 199 days.

(21) Appl. No.: 13/131,387

(22) PCT Filed: Dec. 1, 2009

(86) PCT No.: PCT/EP2009/066170
§ 371 (c)(1),
(2), (4) Date: Aug. 15, 2011

(87) PCT Pub. No.: WO2010/063732
PCT Pub. Date: Jun. 10, 2010

(65) Prior Publication Data
US 2011/0294675 A1  Dec. 1, 2011

(30) Foreign Application Priority Data

Dec. 1, 2008  (EP) .................................. 08170406
Mar. 30, 2009  (EP) .................................. 09156749

(51) Int. Cl.
C12Q 1/68  (2006.01)
C12P 19/34  (2006.01)
C07H 21/00  (2006.01)

(52) U.S. Cl.
USPC ......... 435/6.1; 435/91.1; 435/91.2; 536/23.1; 536/24.3; 536/26.6

(58) Field of Classification Search
USPC ............... 435/6.1, 91.1, 91.2; 536/23.1, 24.3, 536/26.6
See application file for complete search history.

(56) References Cited

PUBLICATIONS

Feuchtenberger, et al., "Semiquantitative and qualitative assessment of B-lymphocyte VH repertoire by a fluorescent multiplex PCR" Journal of Immunological Methods, vol. 276, No. 1-2, May 1, 2003, pp. 121-127.
Li, et al., "Developing of a new multicolor-fluorescent labeled STR amplification kit" Database Medline [Online] US National Library of Medicine, Database accession No. NLM16850595 abstract, vol. 22, No. 2, Apr. 2006, pp. 111-116.
Faulds, et al., "Multiplexed detection of six labeled oligonucleotides using surface enhanced resonance Raman scattering (SERRS)" Analyst, Royal Society of Chemistry, vol. 133, No. 11, Nov. 1, 2008, pp. 1505-1512.
Lazaruk, et al., "Genotyping of forensic short tandem repeat (STR) Systems based on sizing precision in a capillary electrophoresis instrument" Electrophoresis, Wiley Interscience, DE, vol. 19, No. 1, Jan. 1, 1998, pp. 86-93.

(Continued)

Primary Examiner — Jezia Riley
(74) Attorney, Agent, or Firm — Fanelli Haag & Kliger PLLC

(57) ABSTRACT

The present invention relates to combinations of fluorescent dyes used in molecular biology, particularly in multiplex PCR. In particular, the present invention relates to a combination of dyes for amplification reactions, wherein at least four different dyes are used, wherein the first dye is 5-FAM or 6-FAM or a blend thereof, the second dye is selected from the group consisting of DY-530, HEX, CAL Fluor Orange 560 and ATTO 532, the third dye is selected from the group consisting of ATTO 550, DY-555 and DY-556, the fourth dye is selected from the group consisting of ROX, DY-510XL and ATTO 565, and optionally a fifth dye is selected from the group consisting of DY-632 and DY-520XL.

17 Claims, 5 Drawing Sheets

(56) References Cited

PUBLICATIONS

Faulds, et al., "Evaluation of surface-enhanced resonance Raman scattering for quantitative DNA analysis" Analytical Chemistry, American Chemical Society, Vo. 76, No. 2, Jan. 15, 2004, pp. 412-417.

He et al., "On-the-fly fluorescence lifetime detection of dye-labaled DNA primers for multiplex analysis" Analytical Chemistry, vol. 70, No. 16, Aug. 15, 1998, pp. 3413-3418.

Tsuyoshi, et al., "Practical evaluation of universal conditions for four-plex quantitative PCR", Analytical and Bioanalytical Chemistry, Springer, Berlin, DE, vol. 388, No. 1, Mar. 14, 2007, pp. 271-278.

A

B

C

D

E

SEQUENCE LISTING

```
<160> NUMBER OF SEQ ID NOS: 27

<210> SEQ ID NO 1
<211> LENGTH: 21
<212> TYPE: DNA
<213> ORGANISM: Artificial Sequence
<220> FEATURE:
<223> OTHER INFORMATION: PCR primer WB60

<400> SEQUENCE: 1
aataccgcac agatgcgtaa g                                            21

<210> SEQ ID NO 2
<211> LENGTH: 19
<212> TYPE: DNA
<213> ORGANISM: Artificial Sequence
<220> FEATURE:
<223> OTHER INFORMATION: PCR primer WB80

<400> SEQUENCE: 2
gtgcaccata tgcggtgtg                                               19

<210> SEQ ID NO 3
<211> LENGTH: 17
<212> TYPE: DNA
<213> ORGANISM: Artificial Sequence
<220> FEATURE:
<223> OTHER INFORMATION: PCR primer WB94

<400> SEQUENCE: 3
agattgtact gagagtg                                                 17

<210> SEQ ID NO 4
<211> LENGTH: 23
<212> TYPE: DNA
<213> ORGANISM: Artificial Sequence
<220> FEATURE:
<223> OTHER INFORMATION: PCR primer WB100

<400> SEQUENCE: 4
cagagcagat tgtactgaga gtg                                          23

<210> SEQ ID NO 5
<211> LENGTH: 20
<212> TYPE: DNA
<213> ORGANISM: Artificial Sequence
<220> FEATURE:
<223> OTHER INFORMATION: PCR primer WB120

<400> SEQUENCE: 5
ctggcttaac tatgcggcat                                              20

<210> SEQ ID NO 6
<211> LENGTH: 17
```

```
<212> TYPE: DNA
<213> ORGANISM: Artificial Sequence
<220> FEATURE:
<223> OTHER INFORMATION: PCR primer WB140

<400> SEQUENCE: 6
ggtgttggcg ggtgtcg                                                  17

<210> SEQ ID NO 7
<211> LENGTH: 19
<212> TYPE: DNA
<213> ORGANISM: Artificial Sequence
<220> FEATURE:
<223> OTHER INFORMATION: PCR primer WB160

<400> SEQUENCE: 7
ctcgtcaggg tgcgtcagc                                                19

<210> SEQ ID NO 8
<211> LENGTH: 20
<212> TYPE: DNA
<213> ORGANISM: Artificial Sequence
<220> FEATURE:
<223> OTHER INFORMATION: PCR primer WB180

<400> SEQUENCE: 8
ggatgtcggg agcagacaag                                               20

<210> SEQ ID NO 9
<211> LENGTH: 22
<212> TYPE: DNA
<213> ORGANISM: Artificial Sequence
<220> FEATURE:
<223> OTHER INFORMATION: PCR primer WB200

<400> SEQUENCE: 9
gtcacagctt gtctgtaagc gg                                            22

<210> SEQ ID NO 10
<211> LENGTH: 20
<212> TYPE: DNA
<213> ORGANISM: Artificial Sequence
<220> FEATURE:
<223> OTHER INFORMATION: PCR primer WB220

<400> SEQUENCE: 10
acatgcagct ctcggagacg                                               20

<210> SEQ ID NO 11
<211> LENGTH: 22
<212> TYPE: DNA
<213> ORGANISM: Artificial Sequence
<220> FEATURE:
<223> OTHER INFORMATION: PCR primer WB240

<400> SEQUENCE: 11
tgacggtgaa aacctctgac ac                                            22

<210> SEQ ID NO 12
<211> LENGTH: 18
<212> TYPE: DNA
<213> ORGANISM: Artificial Sequence
<220> FEATURE:
<223> OTHER INFORMATION: PCR primer WB260

<400> SEQUENCE: 12
cgtctcgtgc gtttcggt                                                 18
```

<210> SEQ ID NO 13
<211> LENGTH: 20
<212> TYPE: DNA
<213> ORGANISM: Artificial Sequence
<220> FEATURE:
<223> OTHER INFORMATION: PCR primer WB280

<400> SEQUENCE: 13
ggcgtatcac gaagcccttt                                           20

<210> SEQ ID NO 14
<211> LENGTH: 29
<212> TYPE: DNA
<213> ORGANISM: Artificial Sequence
<220> FEATURE:
<223> OTHER INFORMATION: PCR primer WB300

<400> SEQUENCE: 14
gacattaacc tataaaacta ggcgtatca                                 29

<210> SEQ ID NO 15
<211> LENGTH: 30
<212> TYPE: DNA
<213> ORGANISM: Artificial Sequence
<220> FEATURE:
<223> OTHER INFORMATION: PCR primer WB320

<400> SEQUENCE: 15
taagaaacca ttattatcat gacattaacc                                30

<210> SEQ ID NO 16
<211> LENGTH: 23
<212> TYPE: DNA
<213> ORGANISM: Artificial Sequence
<220> FEATURE:
<223> OTHER INFORMATION: PCR primer WB340

<400> SEQUENCE: 16
gaaaagtgcc acctgacgtc taa                                       23

<210> SEQ ID NO 17
<211> LENGTH: 18
<212> TYPE: DNA
<213> ORGANISM: Artificial Sequence
<220> FEATURE:
<223> OTHER INFORMATION: PCR primer WB360

<400> SEQUENCE: 17
ggttccacgc acatttcc                                             18

<210> SEQ ID NO 18
<211> LENGTH: 26
<212> TYPE: DNA
<213> ORGANISM: Artificial Sequence
<220> FEATURE:
<223> OTHER INFORMATION: PCR primer WB380

<400> SEQUENCE: 18
tagaaaaata aacaaatagg ggttcc                                    26

<210> SEQ ID NO 19
<211> LENGTH: 18
<212> TYPE: DNA
<213> ORGANISM: Artificial Sequence
<220> FEATURE:
<223> OTHER INFORMATION: PCR primer Alpha3

```
<400> SEQUENCE: 19
agcctgaatg gcgaatgg                                              18

<210> SEQ ID NO 20
<211> LENGTH: 25
<212> TYPE: DNA
<213> ORGANISM: Artificial Sequence
<220> FEATURE:
<223> OTHER INFORMATION: PCR primer vWA-F

<400> SEQUENCE: 20 tttgcccctta ttattttgtg aactc                                     25

<210> SEQ ID NO 21
<211> LENGTH: 27
<212> TYPE: DNA
<213> ORGANISM: Artificial Sequence
<220> FEATURE:
<223> OTHER INFORMATION: PCR primer vWA-R

<400> SEQUENCE: 21
aggacagatg ataaatacat aggatgg                                    27

<210> SEQ ID NO 22
<211> LENGTH: 25
<212> TYPE: DNA
<213> ORGANISM: Artificial Sequence
<220> FEATURE:
<223> OTHER INFORMATION: PCR primer D12S391-F

<400> SEQUENCE: 22
agtagtttct tctggtgaag gaaga                                      25

<210> SEQ ID NO 23
<211> LENGTH: 25
<212> TYPE: DNA
<213> ORGANISM: Artificial Sequence
<220> FEATURE:
<223> OTHER INFORMATION: PCR primer D12S391-R

<400> SEQUENCE: 23
ctccatatca cttgagctaa ttcct                                      25

<210> SEQ ID NO 24
<211> LENGTH: 21
<212> TYPE: DNA
<213> ORGANISM: Artificial Sequence
<220> FEATURE:
<223> OTHER INFORMATION: PCR primer D18S51-F

<400> SEQUENCE: 24
cgactaccag caacaacaca a                                          21

<210> SEQ ID NO 25
<211> LENGTH: 25
<212> TYPE: DNA
<213> ORGANISM: Artificial Sequence
<220> FEATURE:
<223> OTHER INFORMATION: PCR primer D18S51-R

<400> SEQUENCE: 25
actctgagtg acaaattgag acctt                                      25

<210> SEQ ID NO 26
<211> LENGTH: 21
```

```
<212> TYPE: DNA
<213> ORGANISM: Artificial Sequence
<220> FEATURE:
<223> OTHER INFORMATION: PCR primer D19S433-F

<400> SEQUENCE: 26
gcatgttggc acattcctgt a                                              21

<210> SEQ ID NO 27
<211> LENGTH: 21
<212> TYPE: DNA
<213> ORGANISM: Artificial Sequence
<220> FEATURE:
<223> OTHER INFORMATION: PCR primer D19S433-R

<400> SEQUENCE: 27
tgcacccatt acccgaataa a                                              21
```

COMBINATION OF FLUORESCENT DYES FOR THE DETECTION OF NUCLEIC ACIDS

This application is a National Stage of PCT/EP2009/1066170, filed Dec. 1, 2009 which claims priority to European Patent No. 08170406.6, filed Dec. 1, 2008 and European Patent No. 09156749.5, filed Mar. 30, 2009, the disclosures of which are incorporated herein by reference in their entirety.

TECHNICAL FIELD OF THE INVENTION

The present invention is in the field of molecular biology. Particularly, the present invention relates to the detection of nucleic acids, e.g. in amplification reactions such as polymerase chain reactions (PCR). The present invention is particularly useful in genotyping, quantitative PCR, real-time PCR and multiplex-PCR. The present invention particularly relates to dyes used in PCR.

BACKGROUND OF THE INVENTION

Fluorescent dyes have a wide application in analytical chemistry, biochemistry and molecular biology, such as in DNA sequencing and during detection and amplification of nucleic acids. Fluorescent dyes absorb light of a specific wavelength spectrum ("excitation spectrum") and re-emit energy at a different specific wavelength spectrum ("emission spectrum"). The fluorescent dyes are frequently used as molecular labels attached to DNA and protein probes or other biomolecules.

Multiplex polymerase chain reaction (multiplex PCR) is a PCR technique that enables amplification of two or more products in parallel in a single reaction tube. It is widely used in genotyping applications and different areas of molecular biology, e.g. in research, forensic and diagnostic applications, including human identification and paternity testing and for diagnosis of infectious diseases or chimerism analysis after allogeneic bone marrow transplantation. Multiplex PCR can also be used for qualitative and semi-quantitative gene expression analysis using cDNA as a starting template or in combination with reverse transcription with mRNA as starting material. The nucleic acids analyzed may for example originate from a variety of eukaryotic (human, animal or plant) and prokaryotic (bacterial) or viral sources.

Multiplex PCR is for example used for the simultaneous detection of multiple marker genes and/or their polymorphisms, e.g. single nucleotide polymorphisms (SNPs), short tandem repeats (STRs) or deletion insertion polymorphisms (DIPs or Indels). Detection of the amplification products and their genotyping is usually carried out by multiple colour fluorescence detection after electrophorectic separation (e.g. capillary gel electrophoresis) in DNA sequencers. In real-time, quantitative multiplex PCR, the amplification of multiple target sequences can be monitored at the same time by simultaneous detection of fluorescence of different fluorescent dyes.

Instruments for multiple color fluorescence detection are often designed and calibrated for the combinations of very specific fluorescent dyes, i.e. in terms of excitation and detection spectra and filter sets.

Many DNA sequence analyzers employ a capillary electrophoresis device in combination with a special multiwavelength fluorescence detection system. The basic setup of such instruments was described by Karger et al. (1991) (Karger A, Harris J M, Gesteland R F. Multiwavelength fluorescence detection for DNA sequencing using capillary electrophoresis. Nucleic Acids Res 18, 4955-4962, 1991) and has been put commercially into practice by the ABI Prism® Genetic Analyzer series (310, 3100, 3130 etc.) of Applied Biosystems (Foster City, Calif., USA). These instruments can by used for DNA sequence analysis, multiplex genotyping of genetic polymorphisms (SNPs, DIPs, STRs), mRNA expression analysis or, more generally, for amplified DNA fragment length analysis. The latter is also the current standard for multiplex-PCR STR genotyping in the field of forensics and paternity testing. In this case at least one primer of each primer pair applied during a multiplex amplification is labeled by a covalently bond fluorescent dye at its 5'-OH end or at an internal base. The optical detection units of these instruments use a multiline argon ion laser, adjustable to 10 mW, which excites multiple fluorophores at 488 nm (main wavelength) and 514 nm (Wenz H. Robertson J M, Menchen S, Oaks F, Demorest D M, Scheibler D, Rosenblum B B, Wike C, Gilbert D A, Efcavitch J W. High-precision genotyping by denaturing capillary electrophoresis. Genome Res 8, pp 69-80, 1998). Fluorescence emission is recorded between 525 and 680 nm. The emitted light is separated for simultaneous multiple color fluorescence detection by a spectrograph (prism) and imaged on a cooled CCD (charge coupled device) camera. In the current configurations up to 5 wavelength bands can be defined on the CCD chip by digital band pass filters of app. 10 nm weight. The relative position of these digital band pass filters is proprietarily specified by the manufacturer for a restricted number of dye combinations (see table 1). These settings of the device are also referred to as virtual filter sets. The accurate position and range of the digital band pass filters is not published. The new generation of multi-capillary DNA sequencer such as ABI Prism® 3130 Genetic Analyzer possess in addition also two variable virtual filtersets, termed "any4dyes" or "any5dyes", to allow the customers to adjust preset digital band pass filters for other dye combinations. For this purpose so called condition bound numbers can by varied to some extend. However again, there is no information about the relative position and wavelength range of these digital band pass filters.

TABLE 1

Known fluorescent dye combinations and virtual filtersets for ABI Prism ® Genetic Analyzers.

Fluorescence dye combinations and colour canals

| Blue | Green | Yellow | Red | Orange (far red) | Recommended virtual filterset |
| --- | --- | --- | --- | --- | --- |
| 6-FAM | JOE | TAMRA | ROX | — | F or A |
| 6-FAM | TET | HEX | TAMRA | — | C |
| 5, 6-FAM | JOE | TAMRA | ROX | — | F or A |
| 6-FAM | JOE | NED | ROX | — | F |
| 6-FAM | HEX | NED | ROX | — | F or D |
| 6-FAM | VIC | NED | PET | LIZ | G5 |

5, 6-FAM: 5- and 6-carboxyfluorescein;
6-FAM: 6-carboxyfluorescein;
JOE: 6-carboxy-4'-, 5'-dichloro-2'-, 7'-dimethoxy-fluorescein;
HEX: 4,7,2',4',5',7'-hexachloro-6-carboxy-fluorescein;
TET: 4,7,2',7'-tetrachloro-6-carboxy-fluorescein;
TAMRA: 6-carboxytetramethyl-rhodamine;
VIC: 2'-chloro-7'phenyl-1,4-dichloro-6-carboxy-fluorescein;
NED: 2'-chloro-5'-fluoro-7',8'-benzo-1,4-dichloro-6-carboxyfluorescein;
ROX: 5- and 6-carboxy-X-rhodamin;
PET and LIZ are unpublished proprietary dyes of Applied Biosystems (Foster City, CA, USA).

Furthermore, a spectral calibration must be performed for a selected multi-colour filter set for simultaneous detection of 4 or 5 different colours to generate a mathematical matrix for the correction of overlapping fluorescence emission spectra of the dyes. Mathematical algorithms underlying this calculation are not published.

It is also important to note that the optical setup of ABI Prism® Genetic Analyzers for simultaneous detection of different fluorescent dyes which consists of a single argon ion laser, a spectrograph, virtual filtersets in combination with a CCD-camera and spectral calibration algorithms fundamentally differs from other sequencers or from those used by real-time PCR thermocyclers. The latter possess sets of excitation and emission filters which analyze different dyes by distinct filter combinations and short time offsets (time resolved). Furthermore, the specific optical setup of ABI Prism®Genetic Analyzers also limits the compatibility of different dyes for multi-fluorescence detection.

As outlined in table 1 there are only a few sets of fluorescence dyes available which can be used for DNA oligonucleotide labelling and simultaneous detection by DNA sequencing automates of Applied Biosystems. The relative sensitivity of these dyes dramatically declines between the blue and red colour canal due to the use of a single argon laser which mostly excites at 488 nm. In addition, the relative sensitivity and proper analytical separation of the colours is influenced by spectral overlaps. Further restrictions arise from the fact that many of these dyes (e.g. VIC, HEX, NED, PET, LIZ) are proprietary of Applied Biosystems. Customized PCR primers labelled with the dyes VIC, NED and PET are only available via the synthesis laboratory of this company, and LIZ is only available in combination with a labelled DNA length standard as a commercial product from Applied Biosystems. Furthermore, the chemical structures of PET and LIZ are not known. Thus, there is a need for new colour combinations for technical and economical reasons.

SUMMARY OF THE INVENTION

The present invention is particularly dedicated to combinations of dyes used in DNA sequence analyzers which use a capillary electrophoresis devices in combination with a special multi-wavelength fluorescence detection system. As outlined above, these instruments may, inter alia, by used for DNA sequence analysis, multiplex genotyping of genetic polymorphisms (SNPs, DIPs, STRs), mRNA expression analysis or, more generally, for amplified DNA fragment length analysis.

The present invention relates to alternative combinations of fluorescent dyes for the detection of fluorescently labeled nucleic acids. Surprisingly, it has been found by the present inventors that these combinations have superior properties, e.g. in terms of sensitivity, over the combinations of the prior art. The inventive combinations of fluorescent dyes overcome many of the restrictions and disadvantages of the known combinations. The relative sensitivities of the dyes are increased and the spectral overlap is reduced. As demonstrated by the present inventors in the appended examples, the positive effects of the inventive combinations of dyes cannot be detected from the spectral properties of each dye alone.

In particular, the present invention relates to a method for the simultaneous detection of at least four nucleic acids labelled with a covalently attached dye in a sample comprising the step of detecting the fluorescence emission of said fluorescent dyes upon excitation, wherein a fluorescent dye selected from the group consisting of 5-FAM and 6-FAM or a blend thereof is covalently attached to a first nucleic acid, a fluorescent dye selected from the group consisting of DY-530, HEX, CAL Fluor Orange 560 and ATTO 532 is covalently attached to a second nucleic acid, a fluorescent dye selected from the group consisting of ATTO 550, and DY-556 is covalently attached to a third nucleic acid and a fluorescent dye selected from the group consisting of ROX, DY-510XL and ATTO 565 is covalently attached to a fourth nucleic acid, and optionally a fluorescent dye selected from the group consisting of DY-632 and DY-520XL is covalently attached to a fifth nucleic acid.

The present invention also relates to a kit for multiplex PCR and to a composition comprising:
(i) a first nucleic acid to which a fluorescent dye selected from the group consisting of 5-FAM and 6-FAM or a blend thereof is covalently attached;
(ii) a second nucleic acid to which a fluorescent dye selected from the group consisting of DY-530, HEX, CAL Fluor Orange 560 and ATTO 532 is covalently attached;
(iii) a third nucleic acid to which a fluorescent dye selected from the group consisting of ATTO 550, DY-555 and DY-556 is covalently attached, and
(iv) a fourth nucleic acid to which a fluorescent dye selected from the group consisting of ROX, DY-510XL and ATTO 565 is covalently attached.

Also within the scope of the present invention is the use of a combination of at least four fluorescent dyes in a multiplex polymerase chain reaction, wherein each dye is covalently attached to an oligonucleotide primer substantially complementary to a sequence flanking a locus to be amplified or to an oligonucleotide probe substantially complementary to a sequence on the locus to be amplified and wherein
(i) the first dye is 5-FAM or 6-FAM or a blend thereof,
(ii) the second dye is selected from the group consisting of DY-530, HEX, CAL Fluor Orange 560 and ATTO 532,
(iii) the third dye is selected from the group consisting of ATTO 550 and DY-556,
(iv) the fourth dye is selected from the group consisting of ROX, DY-510XL, and ATTO 565, and consisting of DY-632 and DY-520XL
(v) optionally a fifth dye is selected from the group consisting of DY-632 and DY-520XL.

DETAILED DESCRIPTION OF THE INVENTION

The present invention relates to specific combinations of fluorescent dyes for the detection of fluorescently labeled nucleic acids.

In particular, the present invention relates to a method for the simultaneous detection of at least four nucleic acids labelled with a covalently attached dye in a sample comprising the step of detecting the fluorescence emission of said fluorescent dyes upon excitation, wherein a fluorescent dye selected from the group consisting of 5-FAM and 6-FAM or a blend thereof is covalently attached to a first nucleic acid, a fluorescent dye selected from the group consisting of DY-530, HEX, CAL Fluor Orange 560 and ATTO 532 is covalently attached to a second nucleic acid, a fluorescent dye selected from the group consisting of ATTO 550, DY-555 and DY-556 is covalently attached to a third nucleic acid and a fluorescent dye selected from the group consisting of ROX, DY-510XL and ATTO 565 is covalently attached to a fourth nucleic acid, and optionally fluorescent dye selected from the group consisting of DY-632 and DY-520XL is covalently attached to a fifth nucleic acid.

In one aspect the present invention relates to a method for the simultaneous detection of amplification products from an amplification reaction, comprising the steps of
(i) amplifying three or more loci on nucleic acid templates using primers or pairs of primers substantially complementary to sequences flanking said loci; and
(ii) detecting said amplification products by fluorescence detection of fluorescently labelled amplification products or alternatively by fluorescence detection of fluorescently labelled oligonucleotide probes complementary to sequences on said loci of said amplification products, wherein a fluorescent dye is covalently attached to said amplification product and/or to said oligonucleotide probe and/or to said primer and/or to at least one primer of said primer pair and optionally to a size marker, and wherein at least four different dyes are used, wherein the first dye is 5-FAM or 6-FAM or a blend thereof, the second dye is selected from the group consisting of DY-530, HEX, CAL Fluor Orange 560 and ATTO 532, the third dye is selected from the group consisting of ATTO 550, DY-555 and DY-556, the fourth dye is selected from the group consisting of ROX, DY-510XL and ATTO 565 and optionally a fifth fluorescent dye is selected from the group consisting of DY-632 and DY-520XL.

The invention also pertains to a method for the simultaneous detection of amplification products from a nucleic acid amplification reaction, comprising the steps of
 (i) amplifying three or more nucleic acid sequences using primers or pairs of primers flanking the sequences to be amplified; and
 (ii) detecting either the fluorescently labelled amplification products directly or indirectly using fluorescently labelled oligonucleotide probes complementary to said amplification products
 (iii) optionally detecting a fluorescently labelled size marker,
wherein for each sequence to be detected a distinct fluorescent dye is covalently attached to said amplification product and/or to said oligonucleotide probe and/or to said primer and/or to at least one primer of said primer pair and optionally to a size marker,
and wherein at least four different dyes are used, wherein the first dye is 5-FAM or 6-FAM or a blend thereof, the second dye is selected from the group consisting of DY-530, HEX, CAL Fluor Orange 560 and ATTO 532, the third dye is selected from the group consisting of ATTO 550, DY-555 and DY-556, the fourth dye is selected from the group consisting of ROX, DY-510XL and ATTO 565 and optionally a fifth fluorescent dye is selected from the group consisting of DY-632 and DY-520XL.

In one particular embodiment of the methods of the invention the first dye is 5-FAM or 6-FAM or a blend thereof, the second dye is selected from the group consisting of DY-530 and ATTO 532, the third dye is selected from the group consisting of ATTO 550, DY-555 and DY-556, the fourth dye is selected from the group consisting of DY-510XL and ATTO 565 and optionally a fifth fluorescent dye is selected from the group consisting of DY-632 and DY-520XL.

As outlined above, the invention relate to combinations of at least four different fluorescent dyes. In the context of the above described methods this means that when a size marker fluorescently labelled with one dye of the invention is used, then at least three nucleic acid sequences (i.e. loci) can be amplified and detected, depending on whether a combination of four, five or even more different dyes is used. If no fluorescently labelled size marker is used, than at least four sequences can be amplified and detected.

In the above described method, for each sequence to be amplified (and detected) one particular dye of the combination is designated, allowing for the detection and distinction of each particular amplification product.

"Simultaneous detection" herein means that different dyes can be detected in the same solution, preferably at the same time. Therefore, e.g. a plurality of detectors or filters may be used.

A "locus" in the context of the present invention is a part of the sequence of a nucleic acid, e.g. a chromosome, mRNA, plasmid, cosmid, DNA or RNA (of any origin, e.g. bacterial, viral, eukaryotic, prokaryotic, from plants, fungi or animals, e.g. of human origin) and the like, that is to be amplified and/or detected.

"Amplification products" herein are nucleic acids or oligonucleotides that are the product of an amplification reaction, e.g. of a polymerase chain reaction. They are for example defined by the primers used for amplification.

A "primer" herein refers to an oligonucleotide comprising a sequence that is complementary to a nucleic acid to be amplified or transcribed ("template"). During replication polymerases attach nucleotides to the 3'-OH end of the primer complementary to the respective nucleotides of the template.

An "oligonucleotide" herein refers to a stretch of nucleic acid, e.g. RNA or DNA, that comprises a sequence of two or more nucleotides, e.g. between 2 and 250 nucleotides, more preferably between 2 and 200, even more preferably between 2 and 100, even more preferably between 2 and 30, even more preferably between 2 and 25, even more preferably between 2 and 20, even more preferably between 5 and 25, and most preferably between 10 and 25 nucleotides.

In the first aspect of the method, during amplification detection may for example occur using fluorescently labelled oligonucleotide probes. Alternatively fluorescently labelled primers may be used. In another alternative, fluorescently labelled nucleotides may be used that are incorporated into the amplification products. In this case it is preferred that for every locus to be amplified or detected, the amplification is performed in a separate reaction tube. The amplification products may then be unified for detection.

Thus, detection may in some cases occur during amplification, e.g. after or during each cycle of a polymerase chain reaction and/or after the complete amplification reaction.

In one embodiment of the first aspect of the method, the method additionally comprises the step of separating the amplification products by their size or molecular weight before detecting said amplification products. Separation by size or molecular weight can e.g. be performed using electrophoresis, e.g. gel electrophoresis, or chromatographical techniques.

The amplification reaction is preferably selected from the group comprising polymerase chain reaction (PCR), ligase chain reaction (LCR), transcription-based amplification system (TAS), nucleic acid sequence based amplification (NASBA), rolling circle amplification (RCA), transcription-mediated amplification (TMA), self-sustaining sequence replication (3SR), Qβ amplification and (thermostable) helicase dependent amplification ((t)HAD). More preferably the amplification reaction is a PCR. Most preferably, the amplification reaction is a multiplex PCR, i.e. the amplification of more than one target nucleic acid sequence in a single tube, E.g. 2, 3, 4, 5, 6, 7, 8, 9, 10, 11, 12, 13, 14, 15, 16, 17, 18, 19 or 20 loci (target nucleic acid sequences) may be amplified simultaneously.

As outlined above, the nucleic acid sequences (i.e. the loci) may be amplified simultaneously, e.g. in one reaction tube or separately, e.g. in different reaction tubes. It is so preferred in the methods of the present invention that said loci are amplified simultaneously.

In a particular embodiment of the method for the simultaneous detection of amplification products from an amplification reaction, the amplification reaction is a real-time multiplex polymerase chain reaction and the method comprises the steps of (i) simultaneously amplifying at least four nucleic acid sequences using pairs of primers flanking said sequences t be amplified;

(ii) detecting said amplification products using at least one oligonucleotide probe for each sequence to be amplified, wherein said oligonucleotide probe is substantially complementary to a sequence on said amplification product, wherein a fluorescent dye is covalently attached to each oligonucleotide probe and wherein at least four different dyes are used, wherein the first dye is 5-FAM or 6-FAM or a blend thereof, the second dye is selected from the group consisting of DY-530, HEX, CAL Fluor Orange 560 and ATTO 532, the third dye is selected from the group consisting of ATTO 550, DY-555 and DY-556, the fourth dye is selected from the group consisting of ROX, DY-510XL and ATTO 565 and optionally a fifth fluorescent dye is selected from the group consisting of DY-632 and DY-520XL.

In a preferred embodiment of the methods of the invention, the third dye is ATTO 550 or DY-556. In yet another preferred embodiment the third dye is ATTO 550 or DY-555. In another preferred embodiment the third dye is ATTO 550.

In a preferred embodiment of the methods, the second dye is DY-530, the third dye is ATTO 550 and the fourth dye is selected from the group of ROX and DY-510XL. More preferably the fourth dye is DY-510XL.

When a fifth dye selected from the group consisting of DY-632 and DY-520XL is used, the third dye preferably is ATTO 550 and the fourth dye preferably is selected from the group consisting of DY-510XL and ATTO 565.

In some particular embodiments of the invention at least one dye is covalently attached to an oligonucleotide size marker. In other words, in a preferred embodiment at least one of the nucleic acids is an oligonucleotide size marker. Preferably, said fourth nucleic acid is an oligonucleotide size marker. An oligonucleotide size marker is an oligonucleotide of defined so size or a mixture of oligonucleotides of defined sizes. In case of a mixture, all oligonucleotides of the same size may have the same florescent dye attached or alternatively all oligonucleotides may have the same fluorescent dye attached.

The present invention also relates to a composition comprising:

(i) a first nucleic acid to which a fluorescent dye selected from the group consisting of 5-FAM and 6-FAM or a blend thereof is covalently attached;

(ii) a second nucleic acid to which a fluorescent dye selected from the group consisting of DY-530, HEX, CAL Fluor Orange 560 and ATTO 532 is covalently attached;

(iii) a third nucleic acid to which a fluorescent dye selected from the group consisting of ATTO 550, DY-555 and DY-556 is covalently attached, and (iv) a fourth nucleic acid to which a fluorescent dye selected from the group consisting of ROX, DY-510XL, and ATTO 565 is covalently attached.

In a particular embodiment, the composition additionally comprises:

(v) a fifth nucleic acid to which a fluorescent dye selected from the group consisting of DY-632 and DY-520XL is covalently attached.

Preferably, the third dye is ATTO 550 and the fourth dye is selected from the group consisting of DY-510XL and ATTO 565.

In one embodiment of the composition, each nucleic acid of the composition is a member of the same allelic ladder. In other words, the invention in one aspect relates to allelic ladders which comprise combinations of labelled nucleic acids as described above.

The compositions of the present invention may be used as size markers. In this case each distinct nucleic acid has a defined and known length. Thus, in a preferred embodiment of the composition at least one nucleic acid is an oligonucleotide size marker. Preferably, said fourth nucleic acid is an oligonucleotide size marker.

In one particular embodiment of the compositions of the invention the first dye is 5-FAM or 6-FAM or a blend thereof, the second dye is selected from the group consisting of DY-530, CAL Fluor Orange 560 and ATTO 532, the third dye is selected from the group consisting of ATTO 550, DY-555 and DY-556, the fourth dye is selected from the group consisting of DY-510XL and ATTO 565 and optionally a fifth fluorescent dye is selected from the group consisting of DY-632 and DY-520XL. In a further particular embodiment of the compositions of the invention the first dye is 5-FAM or 6-FAM or a blend thereof, the second dye is selected from the group consisting of DY-530 and ATTO 532, the third dye is selected from the group consisting of ATTO 550, DY-555 and DY-556, the fourth dye is selected from the group consisting of DY-510XL and ATTO 565 and optionally a fifth fluorescent dye is selected from the group consisting of DY-632 and DY-520XL.

The present invention also relates to a kit for multiplex PCR comprising at least four different fluorescent dyes suitable for the covalent attachment to nucleotides, primers, size markers or oligonucleotide probes used in multiplex PCR, wherein the first dye is 5-FAM or 6-FAM or a blend thereof, the second dye is selected from the group of DY-530, HEX, CAL Fluor Orange 560 and ATTO 532, the third dye is selected from the group consisting of ATTO 550, DY-555 and DY-556, the fourth dye is selected from the group consisting of ROX, DY-510XL and ATTO 565 and optionally a fifth fluorescent dye is selected from the group consisting of DY-632 and DY-520XL.

In a further aspect the present invention relates to a kit for multiplex PCR comprising (i) at least one first nucleic acid to which a fluorescent dye selected from the group consisting of 5-FAM and 6-FAM or a blend thereof is covalently attached;

(ii) at least one second nucleic acid to which a fluorescent dye selected from the group consisting of DY-530, HEX, CAL Fluor Orange 560 and ATTO 532 is covalently attached;

(iii) at least one third nucleic acid to which a fluorescent dye selected from the group consisting of ATTO 550, DY-555 and DY-556 is covalently attached, and (iv) at least one fourth nucleic acid to which a fluorescent dye selected from the group consisting of ROX, DY-510XL, and ATTO 565 is covalently attached.

In particular embodiments of the kits of the invention, the first, second, third and/or fourth nucleic acid may be a probe. One or more of these nucleic acids may also be a size marker.

In particular, the present the kit of the present invention is a kit for multiplex PCR according comprising:

(i) at least three different pairs of primers, wherein to at least one primer of each pair a fluorescent dye is covalently attached; and (ii) optionally an oligonucleotide size marker, wherein a fluorescent dye is covalently attached to said size marker;

wherein at least four different fluorescent dyes are used and wherein the first dye is 5-FAM or 6-FAM or a blend thereof, the second dye is selected from the group of DY-530, HEX, CAL Fluor 560 and ATTO 532, the third dye is selected from the group consisting of ATTO 550, DY-555 and DY-556, the fourth dye is selected from the group consisting of ROX, DY-510XL and ATTO 565 and optionally a fifth fluorescent dye is selected from the group consisting of DY-632 and DY-520XL.

In a preferred embodiment the kit comprises at least five different fluorescent dyes, wherein the third dye is ATTO 550 and the fourth dye is selected from the group consisting of DY-510XL and ATTO 565.

In one particular embodiment of the kits of the invention the first dye is 5-FAM or 6-FAM or a blend thereof, the second dye is selected from the group consisting of DY-530, CAL Fluor Orange 560 and ATTO 532, the third dye is selected from the group consisting of ATTO 550, DY-555 and DY-556, the fourth dye is selected from the group consisting of DY-510XL and ATTO 565 and optionally a fifth fluorescent dye is selected from the group consisting of DY-632 and DY-520XL. In yet another particular embodiment of the kits of the invention the first dye is 5-FAM or 6-FAM or a blend thereof, the second dye is selected from the group consisting of DY-530 and ATTO 532, the third dye is selected from the group consisting of ATTO 550, DY-555 and DY-556, the fourth dye is selected from the group consisting of DY-510XL and ATTO 565 and optionally a fifth fluorescent dye is selected from the group consisting of DY-632 and DY-520XL.

Also within the scope of the present invention is the use of a combination of at least four fluorescent dyes in a multiplex polymerase chain reaction, wherein each dye is covalently attached to an oligonucleotide primer substantially complementary to a sequence flanking a locus to be amplified or to an oligonucleotide probe substantially complementary to a sequence on the locus to be amplified and wherein
(i) the first dye is 5-FAM or 6-FAM or a blend thereof,
(ii) the second dye is selected from the group consisting of DY-530, HEX, CAL Fluor Orange 560 and ATTO 532,
(iii) the third dye is selected from the group consisting of ATTO 550, DY-555, and DY-556,
(iv) the fourth dye is selected from the group consisting of ROX, DY-510XL, and ATTO 565, and consisting of DY-632 and DY-520XL
(v) optionally a fifth dye is selected from the group consisting of DY-632 and DY-520XL.

In one embodiment of the use according to the invention, the third dye is ATTO 550 or DY-556. In one embodiment of the use, the third dye is ATTO 550.

In another embodiment of the use according to the present invention the third dye is ATTO 550 and the fourth dye is selected from the group consisting of DY-510XL and ATTO 565.

In another embodiment of the use of the present invention, the second dye is DY-530, the third dye is ATTO 550 and the fourth dye is selected from the group of ROX and DY-510XL.

When a fifth dye is selected from the group consisting of DY-632 and DY-520XL is used, it is preferred that the second dye is DY-530, the third dye is ATTO 550 and the fourth dye is DY-510XL.

In one particular embodiment of the use of a combination of at least four fluorescent dyes the first dye is 5-FAM or 6-FAM or a blend thereof, the second dye is selected from the group consisting of DY-530, CAL Fluor Orange 560 and ATTO 532, the third dye is selected from the group consisting of ATTO 550, DY-555 and DY-556, the fourth dye is selected from the group consisting of DY-150XL and ATTO 565 and optionally a fifth fluorescent dye is selected from the group consisting of DY-632 and DY-520XL. In a further particular embodiment of the use of a combination of at least four fluorescent dyes the first dye is 5-FAM or 6-FAM or a blend thereof, the second dye is selected from the group consisting of DY-530 and ATTO 532, the third dye is selected from the group consisting of ATTO 550, DY-555 and DY-556, the fourth dye is selected from the group consisting of DY-510XL and ATTO 565 and optionally a fifth fluorescent dye is selected from the group consisting of DY-632 and DY-520XL.

In some embodiments of the use according to the present invention one dye is covalently attached to an oligonucleotide size marker.

The methods, kits and compositions of the present invention may also be used in the context of forensics and paternity testing.

The structures of 5-FAM (5-carboxyfluorescein) and 6-FAM (6-carboxyfluorescein), HEX (6-carboxy-2',4,4',5',7,7'-hexachlorofluorescein), VIC (2'-chloro-7'phenyl-1,4-dichloro-6-carboxyfluorescein), NED (2'-chloro-5'-fluoro-7',8-benzo-1,4-dichloro-6-carboxyfluorescein) and ROX (5-carboxy-X-rhodamine) are disclosed in U.S. Pat. No. 6,316,610 and EP 1 155 027 B1 (see FIGS. 3 to 5 of U.S. Pat. No. 6,316,610 B2 and EP 1 155 027 B1). The structures of DY-530, DY-556, DY-510XL, DY-632 and DY-520XL are illustrated in appended FIGS. 1A-E, respectively. The structures of ATTO 565 is illustrated in appended FIG. 2. The structures of the phosphoramidites of CAL Fluor 560 Orange, CAL Fluor Red 590, CAL Fluor Red 610 and CAL Fluor Red 635 are shown in appended FIGS. 3 A-D, respectively. The structure of DY-555 is illustrated in FIG. 5. DY-530, DY-556, DY-510XL, DY-632 and DY-520XL are products of Dyomics GmbH, Jena, Germany. ATTO 532, ATTO 550 and ATTO 565 are products of ATTO-TEC GMBH, Siegen, Germany. VIC, NED, PET and LIZ are products of Applied Biosystems, Foster City, Calif., USA. CAL Fluor 560 Orange, CAL Fluor Red 590, CAL Fluor Red 610 and CAL Fluor Red 635 are products of Biosearch Technologies Inc., Novato, Calif., USA.

The attachment of the dyes to nucleotides, primers, probes and/or markers in the context of the present invention can be achieved via standard coupling reactions known to the skilled person, e.g. via N-hydroxysuccinimide (NHS) ester or phosphoramidite coupling.

The specific combinations of fluorescence dyes according to the present invention may be used with DNA sequencing automates of the ABI Prism® Genetic Analyzer series (310, 3100, 3130 etc.) of Applied Biosystems (Foster City, Calif., USA). Other electrophoresis instruments which use the same optical configuration for a multi-wavelength detection unit are also possible. Furthermore, conventional real-time PCR instruments, e.g. instruments of the ABI Prism® Sequence Detection System (SDS) series of Applied Biosystems, the Mx series of Stratagene (La Jolla, Calif., USA) or the Mastercycler® ep realplex (Eppendorf, Hamburg, Germany) are possible.

The fluorescence dyes 6-FAM, VIC, NED, PET or ROX and LIZ are according to Applied Biosystems the most recommended once in multi-wavelength detection assays for the blue, green, yellow, red and orange colour channel, respectively. The specific combinations of fluorescence dyes according to the present invention have compared with the combinations known in the art, the following technical advantages as demonstrated in the appended example 3. Advantages of the inventive combinations of dyes, particularly in terms of relative sensitivities are demonstrated in table 4 of example 3. As compared to the combinations of dyes known in the art better sensitivities were achieved, particularly ATTO 532, DY-530 and CAL Fluor Orange 560 were better than combinations with VIC. Comparably, ATTO 550 gave better results than NED and DY-510XL was better than PET. Thus, new dye combinations were found which improved considerably the sensitivity of green, yellow and red labelled PCR amplicons. This provides more flexibilities for the design of sensitive multiplex PCR, especially in the field of forensic (e.g. detection of stains) and clinical applications (e.g. cancer and per-natal diagnostics). The new green, yellow and red dyes can also be used in combination with known compatible dyes, e.g. the combination 6-FAM, VIC, ATTO 550 and ROX or 6-FAM, VIC, ATTO 550, PET and DY-632 (data not shown). Further combinations are possible.

Furthermore, the dyes DY-632 and DY-520XL were identified for the synthesis of new internal length standards to substitute LIZ. Example 2 and 4 shows for DY-632 the feasibility of such a standard in the range of 60 to 380 bp with 20 bp increments.

As demonstrated in examples 1 and 3, it is not possible to conclude from looking at the spectral data (e.g. absorption and emission maxima, extinction coefficient) of fluorescent dyes to their suitability for the use in combinations of dyes for the detection of multiple nucleic acids. The selection of specific combinations of fluorescent dyes cannot be deducted from the spectral properties of each dye alone.

As outlined above the detection unit of ABI Prism® Genetic Analyzers possess a unique setup. The optical specification of the instruments is not completely published (e.g. exact position of digital bandpass filters within virtual filter-sets, algorithm for the correction of overlapping fluorescence emission spectra of the dyes). No spectral data for fluorescence dyes exist until hitherto which have been recorded under electrophoretic conditions at the detection unit of DNA sequence automates, in particular those from Applied Biosystems. Thus, compatible dye combinations for ABI Prism® Genetic Analyzers cannot be selected by standardized published optical characteristics of the dyes (excitation and emission maxima, quantum yields etc.) or recommendations for other instruments (e.g. real-time thermocyclers), but must be evaluated under the appropriate running (buffer, pH) and detection conditions (virtual filter sets, spectral calibration) (see example 1). Furthermore, it must be ensured that covalently labelled PCR amplicons give a single fragment peak with precise size resolution in capillary electrophoresis. This is sometimes not the case for fluorescence dyes which are only available as mixtures of diastereoisomers. Interestingly and unexpectedly with regard to this fact, the dye ATTO 550 which is described by the manufacturer as a mixture of three diastereoisomers gave apparently single amplicon peak in the range of 50-400 base. Finally, all dyes must be chemically and physically stable under all conditions applied (e.g. oligonucleotide synthesis, oligonucleotide purification, PCR and capillary electrophoresis). This variety of imponderabilities had to be empirically assessed. For this purpose a new PCR based evaluation assay for dye combinations was elaborated (example 3).

EXAMPLES

Example 1

Figure 1:
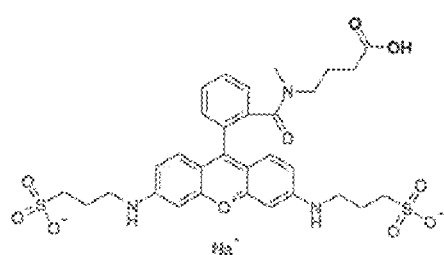
FIG. 1: Structures of fluorescence dyes from Dyomics GmbH (Jena, Germany).(A) DY-530 free carboxylic acid, (B) DY-556 NHS-ester, mono-sodium salt), (C) DY-632 free acid, di-sodium salt), (D) DY-510XL free carboxylic acid, (E) DY-520XL, carboxylic acid. In case of (A), (C), (D) and (E) free carboxyl groups are used for NHS-coupling to the 5'-ends of oligonucleotides.
Figure 1:
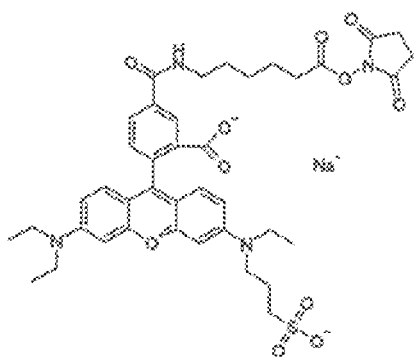
Figure 1:
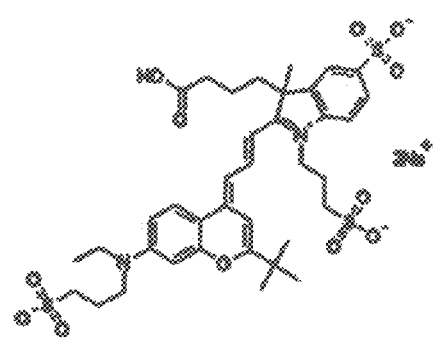
Figure 1:
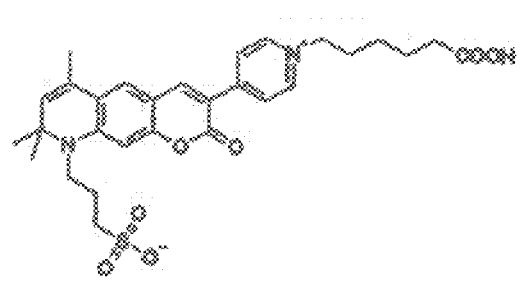
Figure 1:
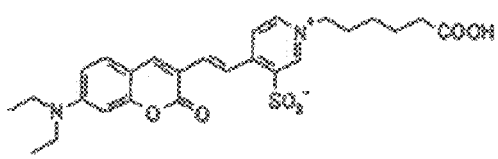
Figure 2:
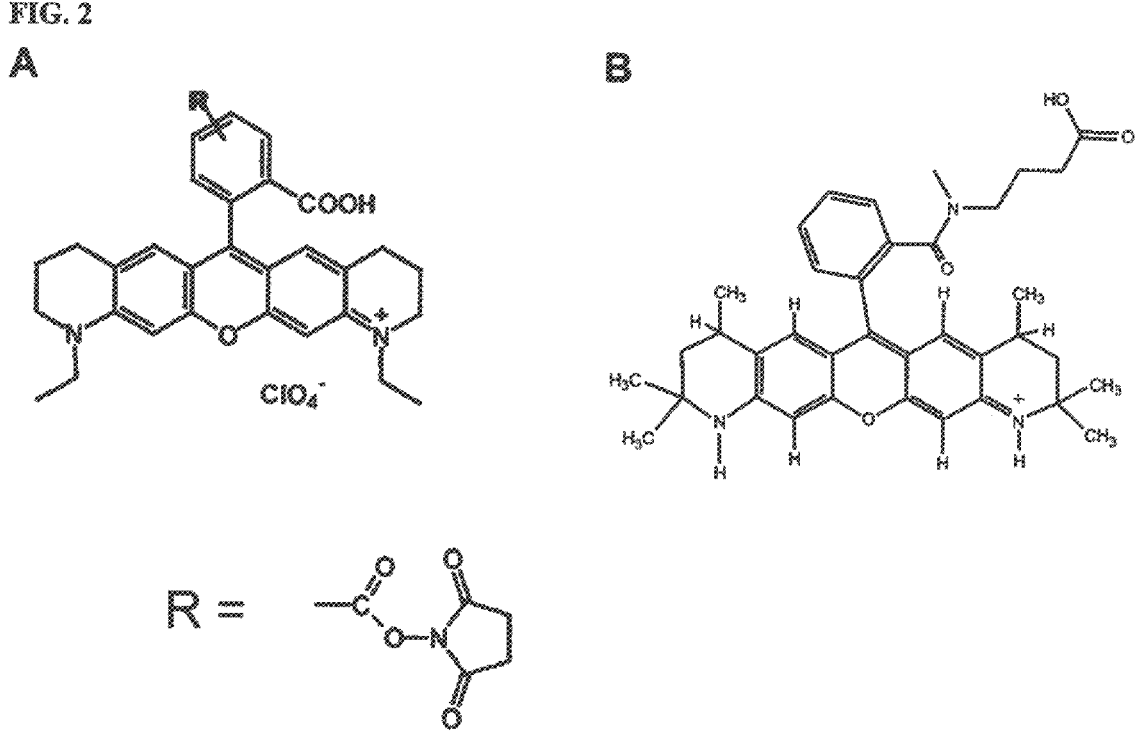
FIG. 2: Structures of fluorescence dyes from ATTO-TEC GMBH (Siegen, Germany). (A) ATTO 565 (perchlorate) NHS-ester, (B) ATTO 550, free acid of one diasteriomer. The free carboxyl group is used for NHS-coupling to the 5'-ends of oligonucleotides.
Figure 3:
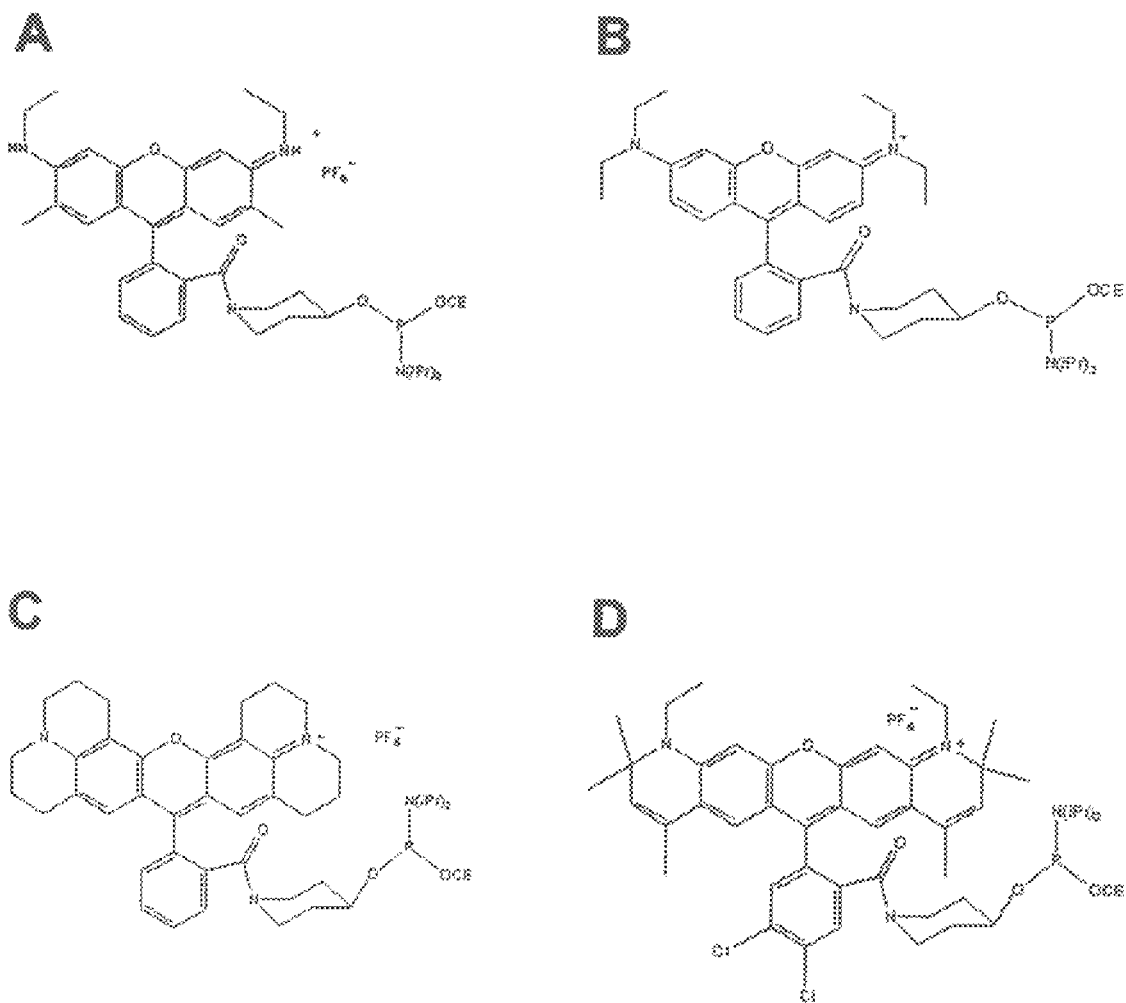
FIG. 3: Structures of fluorescence dye amidites from Biosearch Technologies Inc. (Novato, Calif., USA). (A) CAL Floor Orange 560, (B) CAL Fluor Red 590, (C) CAL Fluor Red 610, (D) CAL Fluor Red 635. iPr: isopropyl, CE: 3-cyanoethyl.

Recording Spectral Data of Fluorescent Dye Labelled Oligonucleotides Dissolved in Electrophoresis Buffer The spectral characteristics of fluorescent dyes are considerably influenced by the solvent system, buffer composition and the pH-values. As a general rule, published spectral data of uncoupled fluorescence dyes have been recorded by the dye manufacturers in water or organic solvents like methanol, ethanol, dimethylformamide or dimethylsulfoxide. Rarely, data are available which have been measured in defined PCR-buffers, and no data exist until hitherto which have been recorded under electrophoretic conditions at the detection unit of DNA sequence automates, in particular those from Applied Biosystems (Foster City, Calif., USA) which are in the focus of this invention. In addition, it is known that spectral characteristics of fluorescent dyes may alter after coupling to oligonucleotides.

The oligonucleotide primers were synthetisized by standard phosphoramidite chemistry at service laboratories (e.g. Eurogentec SA, Seraing, Belgium; Applied Biosystems, Foster City, Calif., USA). Fluorescent dyes were covalently linked to the 5'-end of oligonucleotides via N-hydroxysuccinimide (NHS) ester coupling (Giusti W G, Adriano T. Synthesis and characterization of 5'-fluorescent-dye-labeled oligonucleotides. PCR Methods Appl 2:223-227, 1993) or standard phosphoramidite chemistry (Theisen P, McCollum C, Andrus A. Fluorescent dye phosphoramidite labelling of oligonucleotides. Nucleic Acids Symp Ser 27, pp. 99-100, 1992). All primers were purified at the service laboratories by ion pair reversed phase high performance liquid chromatography or polyacrylamide gel electrophoresis according to standard protocols, dissolved in TE-buffer (10 mM Tris/HCl pH 8.0, adjusted at room temperature, 1 mM EDTA) to 100 µMolar and stored at 4° C. in the dark until further use.

The oligonucleotides were diluted 20fold and 2000fold for UV/Vis spectroscopic and fluorometric measurements, respectively, in capillary electrophoresis gel buffer of ABI Prism® Genetic Analyzers which consisted of 100 mM N-[tris-(hydroxymethyl)-methyl-3-amino]-propane sulfonic acid (TAPS)/NaOH (pH 8.0, adjusted at room temperature), 8 Molar urea and 5% 2-pyrrolidone (Rosenblum B B, Oaks F, Menchen S, Johnson B. Improved single-strand DNA sizing accuracy in capillary electrophoresis. Nucleic Acids Res, 25, pp. 3925-3929, 1997). The absorbance spectra were recorded with a SPECORD®S 100 Bio UV/VIS-spectrophotometer (Analytik Jena AG, Jena, Germany) between 200 nm and 700 mm. A SPEX® Fluorolog®-3 spectrofluorometer (HORIBA Jobin Yvon Inc, Edison, N.Y., USA) was used to analyse fluorescence spectra. An excitation wavelength of 488 nm which corresponded to the main emission wave length of the argon laser of ABI Prism® Genetic Analyzers was used and the emission spectra were recorded between 520 nm and 700 nm.

ated for each dye combination and each DNA sequence analyzer of Applied Biosystems. The spectral calibration creates for a selected multi colour filter set (simultaneous detection of 4 or 5 different colours) a mathematical matrix to correct the overlapping of fluorescence emission spectra of the dyes. Matrix standard sets for ABI Prism® 310 Genetic Analyzer consists of mixtures of at least 5 labelled PCR amplicon fragments for every colour, respectively, which should be clearly separated in capillary electrophoresis and should give signal heights of approximately 1000 to 3000 relative fluorescent units (RFUs). Thus, 4 or 5 different labelled fragment mixtures, respectively, are needed for this type of instrument. In contrast, matrix standards for ABI Prism® 3130 or 3130XL Genetic Analyzer consists of one mixture of different labelled PCR amplicon fragments in all colours of a defined colour combination (4 or 5), which should be clearly

TABLE 2

Emission maxima and relative heights of different fluorescence dyes at their emission maxima.

| Fluorophore name | Colour canal of ABI Prism® Genetic Analyzer | Absorption maximum [nm] | | Emission maximum [nm] | | Signal height [RFU] | Relative signal height [%] |
|---|---|---|---|---|---|---|---|
| | | Literature | Measured | Literature | Measured | | |
| 6-FAM | blue | 495 | 499 | 520 | 519 | 3017361 | 100.0 |
| VIC | green | 538 | 534 | 554 | 552 | 1812883 | 60.1 |
| ATTO 532 | green | 532 | 537 | 553 | 553 | 1220612 | 40.5 |
| DY-530 | green | 539 | 538 | 561 | 555 | 607600 | 20.1 |
| HEX | green | 535 | 543 | 556 | 557 | 421510 | 14.0 |
| CAL Fluor Orange 560 | | 537 | 539 | 558 | 557 | 594053 | 19.7 |
| DY-548 | yellow | 558 | 555 | 572 | 564 | 206473 | 6.8 |
| NED | yellow | 546 | 552 | 575 | 572 | 258383 | 8.6 |
| ATTO 550 | yellow | 554 | 560 | 576 | 576 | 344008 | 11.4 |
| DY-556 | yellow | 548 | 562 | 573 | 583 | 163480 | 5.4 |
| DY-510XL | red | 509 | 511 | 590 | 584 | 265057 | 8.8 |
| CAL Fluor Red 590 | red | 569 | 570 | 591 | 587 | 66327 | 2.2 |
| PET | red | 558 | 560 | 595 | 587 | 166181 | 5.5 |
| ATTO565 | red | 563 | 573 | 592 | 594 | 149450 | 5.0 |
| CAL Fluor Red 610 | red | 590 | 592 | 610 | 604 | 62312 | 2.1 |
| ROX | red | 587 | 588 | 607 | 606 | 51467 | 1.7 |
| Texas Red | red | 586 | 596 | 605 | 610 | 52877 | 1.8 |
| CAL Fluor Red 635 | orange | 616 | 616 | 637 | 630 | 13898 | 0.5 |
| DY-632 | orange | 637 | 632 | 657 | 657 | 48445 | 1.6 |
| DY-520XL | orange | 520 | 541 | 664 | 666 | 25006 | 0.8 |

The dye-labelled oligonucleotides (primer WB 94, DNA sequence 5'-[DYE]-AGATTGTACTGAGAGTG-3') were dissolved at the same concentration in capillary electrophoresis gel buffer of ABI Prism ® Genetic Analyzer. An excitation wavelength of 488 nm was used. The measured excitation and emission maxima were compared with data available from the literature. The signal heights (RFU, relative fluorescence units) were recorded at the emission maxima. The signal height for 6-FAM was set 100% to calculate relative signal heights.

The results of the measurements using dyes linked to the 5'-end of the primer WB 94 (DNA sequence 5'-[DYE]-AGATTGTACTGAGAGTG-3') are summarized in table 2. Dye-specific differences between published and measured excitation maxima of up to 21 nm (DY-520XL) and emission maxima of up to 10 nm (DY-556) could be observed. The results were not predictable from published data.

Example 2

Setting Up of Colour Matrix Standards for the Spectral Calibration of ABI Prism® 310 Genetic Analyzer and ABI Prism® 3130 Genetic Analyzer Prior to any analysis of labelled DNA fragment size a spectral calibration with fluorescent labels has to be generated for each dye combination and each DNA sequence analyzer of Applied Biosystems. The spectral calibration creates for a selected multi colour filter set (simultaneous detection of 4 or 5 different colours) a mathematical matrix to correct the overlapping of fluorescence emission spectra of the dyes.

separated in capillary electrophoresis and should give signal heights of approximately 1000 to 3000 RFUs.

Matrix standard sets were prepared by PCR. All reagents and other consumables used were of PCR quality, particularly free of DNA, DNA- and RNA-dependent nucleases. PCR primers were synthetisized and purified as outlined in Example 1. Plasmid pUC19 (1 µg) (Yanisch-Perron C, Vieira J, Messing J. Improved MI3 phage cloning vectors and host strains: nucleotide sequences of the M13 mp18 and pUC19 vectors. Gene, 33, pp. 103-119, 1985) was linearized with the DNA restriction endonuclease Aat II (New England Biolabs, Ipswich, Mass., USA; applied according to the instruction of the manufacturer), purified (QIAquick PCR purification kit, Qiagen, Hilden Germany; applied according to the instruction of the manufacturer), and quantified by UV-VIS spectrometry at 260 nm (Sambrook J, Fritsche E F, Maniatis T.

Molecular cloning. A laboratory manual. 2$^{nd}$ edition, Cold Spring Harbor Laboratory Press, 1989). PCR primer were designed (table 3) to give amplicons from 60 bp to 300 bp with 20 bp increments. The PCR primer termed Alpha 3 was labelled at its 5'-end with the respective fluorescence dye and combined in monoplex PCRs with one of the primers WE 80 to WB300, respectively.

TABLE 3

PCR primers for matrix and length standards.

| Primer name | DNA sequence (5'→3') | Amplicon size [bp] combined in PCR with primer Alpha 3 |
|---|---|---|
| WB 60 | AATACCGCACAGATGCGTAAG | 60 |
| WB 80 | GTGCACCATATGCGGTGTG | 80 |
| WB 100 | CAGAGCAGATTGTACTGAGAGTG | 100 |
| WB 120 | CTGGCTTAACTATGCGGCAT | 120 |
| WB 140 | GGTGTTGGCGGGTGTCG | 140 |
| WB 160 | CTCGTCAGGGTGCGTCAGC | 160 |
| WB 180 | GGATGTCGGGAGCAGACAAG | 180 |
| WB 200 | GTCACAGCTTGTCTGTAAGCGG | 200 |
| WB 220 | ACATGCAGCTCTCGGAGACG | 220 |
| WB 240 | TGACGGTGAAAACCTCTGACAC | 140 |
| WB 260 | CGTCTCGTGCGTTTCGGT | 260 |
| WB 280 | GGCGTATCACGAAGCCCTTT | 280 |
| WB 300 | GACATTAACCTATAAAACTAGGCGTATCA | 300 |
| WB320 | TAAGAAACCATTATTATCATGACATTAACC | 320 |
| WB340 | GAAAAGTGCCACCTGACGTCTAA | 340 |
| WB360 | GGTTCCACGCACATTTCC | 360 |
| WB380 | TAGAAAAATAAACAAATAGGGGTTCC | 380 |
| Alpha 3 | AGCCTGAATGGCGAATGG | – |

Primer Alpha 3 was labelled at its 5'-end with the respective fluorescence dye.

The enzyme reaction contained in a total volume of 25 µL 50 mM Tris/HCl (pH 8.8; adjusted at room temperature), 20 mM NH$_4$SO$_4$, 0.2 mM dNTPs (equimolar mixture of dATP, dCTP, dGTP, dTTP), 1.5 mM MgCl$_2$, 1.5 Units JumpStart™ Taq DNA polymerase (Sigma-Aldrich Chemie GmbH, Taufkirchen, Germany), 200 µg/mL bovine serum albumin (Roche Diagnostics GmbH, Mannheim, Germany), 0.01% Tween 20, 200 nM primers, and 1.0 pg linearized plasmid DNA. An ABI 9600 (Applied Biosystems, Foster City, Calif., USA) thermocycler was used. The cycling conditions consisted of an initial thermal activation of 240 s at 95° C., followed be 30 cycles of 30 s denaturation at 94° C., 120 s primer annealing at 60° C. and 75 s primer extension at 72° C. The ramp speed was set to 1° C./s for all temperature changes. Afterwards a final elongation step of 3600 s at 68° C. was performed to maximize the template independent addition of one nucleotides at the 3'-end (preferentially A) due to the intrinsic terminal transferase activity of Taq DNA polymerase. The PCR products were purified and quantified as outlined above. Dilutions of the PCR products were done in TE buffer (1 mM Tris/HCl pH 8.0, adjusted at room temperature; 0.1 mM EDTA). Aliquotes of 1 µL of the purified PCR products were withdrawn and mixed with 12.5 µL HiDi™ formamide (Applied Biosystems). The samples were denaturated for 3 min at 95° C., chilled to 10° C. and stored at room temperature prior electrophoresis. An ABI Prism® 310 or 3130 Genetic Analyzer (Applied Biosystems) was used to separate PCR fragments by capillilary electrophoresis. The samples were injected electrocinetically (10 s at 15,000 V or 3,000 V for ABI Prism® 310 or 3130 Genetic Analyzer, respectively). The electrophoretic run conditions were as follows: A single capillary (ABI Prism® 310 Genetic Analyzer) or a capillary array with 4 capillaries (ABI Prism® 3130 Genetic Analyzer) (50 µm internal diameter, app. 40 cm length) filled with POP-4 [4% poly-(N,N-dimethylacrylamid), 8 M urea, 5% 2-pyrrolidone, 100 mM (hydroxymethyl)-methyl-3-aminopropan-sulfonic acid (TAPS)/NaOH pH 8.0, adjusted at room temperature; Applied Biosystems], at 60° C. and 15.000 Volt for 25 min. In case of the ABI Prism® 310 Genetic Analyzer the filtersets D or G5 were applied for the simultaneous detection of 4 or 5 dyes, respectively. In case of the ABI Prism® 3130 Genetic Analyzer the filter sets "any4dyes" or "any5dyes" were applied for the simultaneous detection of the 4 or 5 colours, respectively. The software Genmapper® (Applied Biosystems, Foster City, Calif., USA) was used to calculate peak heights. Then appropriate dilutions of the PCR products were made and mixed to achieve matrix standards with app. 1000-3000 RFU peak heights. Matrix files were then recorded with the appropriate spectral calibration software module of the data collection software of the DNA sequencing automates and stored for subsequent analyses.

Multiple fragment matrix standards for ABI Prism®310 Genetic Analyzers which were labelled with ROX, DY-632 and DY-520XL could be also applied as internal length standards (see example 4). In some embodiments, further dye-labelled PCR amplicons using the PCR primers WB 320, WB 340, WB 360 and WB 380 (see table 1), respectively, in combination with the PCR primer Alpha 3 were added to these matrix standards to extend the range of the length standards.

Example 3

Evaluation of New Fluorescence Dye Combinations for ABI Prism® Genetic Analyzers The series of ABI Prism® Genetic Analyzer is dedicated and validated for high precision separation of labelled single stranded DNA for DNA sequencing or DNA fragment size analysis. The instruments are not qualified for absolute quantification. For the means of peak heights relative standard deviations (68% confidence) of 12% or more are frequently observed when performing run-to-run precision experiments. The capillaries are filled with new buffered polymer solution for every run. In addition, noteworthy sensitivity differences exist between the instruments. Due to these variations an assay with internal normalisation was elaborated for the evaluation of new fluorescence dye combinations. For this purpose a PCR was designed which allowed to label both strands of an amplicon.

Primers were synthesized and purified as outlined in example 1. Linearized and purified plasmid pUC19 as outlined in example 2 was used as template DNA. One DNA strand of the PCR amplicon was labelled at its 5'-end with the dye of interest using the primer WB 94 (DNA sequence 5'-[DYE]-AGATTGTACTGAGAGTG-3'). The other DNA strand of the amplicon comprised the primer Alpha 3FAM (DNA sequence 5'-[6-FAM]-TTTTTT-[HEG]-AGCCT-GAATGGCGAATGG) with 6-FAM as universal normalization dye standard. In addition, Alpha 3FAM contained 5' to its template specific sequence five thymidine residues bridged via an internal hexaethylene glycol (HEG) moiety which functions as a terminator of Taq DNA polymerase (Newton C R, Holland D, Heptinstall L E, Hodgson I, Edge M D, Markham A F, McLean M J. The production of PCR products with 5' single-stranded tails using primers that incorporate novel phosphoramidite intermediates. Nucleic Acids Res, 21, pp 1155-1162, 1993). Thus, the DNA strand which contained Alpha 3FAM was significantly larger than the DNA strand with the fluorescence dye of interest and both strands could be clearly separated by capillary electrophoresis. PCR, PCR purification and capillary electrophoresis were performed as described in example 2.

The samples were analysed after capillary electrophoresis using the software GeneScan® Analysis and GeneMapper® with the corresponding matrix files (see example 2). The peak areas of the DNA strand labelled with the dye of interest was normalized by the 6-FAM signal of the complementary DNA strand, whereas the 6-FAM signal was set to 100%. The results for selected dye combinations are summarized in table 4.

Example 4

A Multiplex PCR for the Detection of Four STR-Loci with Overlapping Fragment Size Ranges Using a New 5 Colour Combination for ABI Prism® Genetic Analyzers A multiplex PCR for the genotyping of four STR loci with overlapping fragment size ranges was elaborated to test the usability of one new fluorescence dye combination.

Basic molecular genetic experiments were done according to Sambrook et al. (1989) (Sambrook J, Fritsche E F, Maniatis T. Molecular cloning. A laboratory manual. $2^{nd}$ edition, Cold Spring Harbor Laboratory Press, 1989). Human test specimens were whole blood or sputum, the latter of which was collected with sterile buccal swabs (Nerbe Plus GmbH, Winsen/Luhe, Germany) according to the instructions of the manufacturer. DNA was extracted using the NucleoSpin®Tissue kit (Macherey & Nagel, Dueren, Ger-

TABLE 4

Evaluation of new fluorescence dye combinations for ABI Prism ® Genetic Analyzers.

| Zeilen - Nr. | ABI Prism ® Genetic Analyzer | Virtual filter set | Dye combination 1 | 2 | 3 | 4 | 5 | Relative sensitivity [%] 1 | 2 | 3 | 4 | 5 |
|---|---|---|---|---|---|---|---|---|---|---|---|---|
| 1 | 310 | D | 6-FAM | VIC | NED | ROX | — | 100 | 143 | 16 | 21 | — |
| 2 | 310 | D | 6-FAM | VIC | TAMRA | ROX | — | 100 | 141 | 37 | 18 | — |
| 3 | 310 | D | 6-FAM | JOE | TAMRA | ROX | — | 100 | 55 | 37 | 18 | — |
| 4 | 310 | D | 6-FAM | HEX | NED | ROX | — | 100 | 78 | 16 | 21 | — |
| 5 | 310 | D | 6-FAM | HEX | TAMRA | ROX | — | 100 | 141 | 36 | 18 | — |
| 6 | 310 | D | 6-FAM | HEX | ATTO 550 | ROX | — | 100 | 78 | 77 | 22 | — |
| 7 | 310 | D | 6-FAM | HEX | DY-556 | ROX | — | 100 | 78 | 11 | 22 | — |
| 8 | 310 | D | 6-FAM | HEX | DY-548 | ROX | — | 100 | 78 | 16 | 22 | — |
| 9 | 310 | D | 6-FAM | DY-530 | NED | ROX | — | 100 | 145 | 16 | 22 | — |
| 10 | 310 | D | 6-FAM | DY-530 | TAMRA | ROX | — | 100 | 157 | 37 | 18 | — |
| 11 | 310 | D | 6-FAM | DY-530 | ATTO 550 | ROX | — | 100 | 145 | 77 | 22 | — |
| 12 | 310 | D | 6-FAM | ATTO 532 | NED | ROX | — | 100 | 149 | 16 | 22 | — |
| 13 | 310 | D | 6-FAM | ATTO 532 | ATTO 550 | ROX | — | 100 | 149 | 77 | 22 | — |
| 14 | 310 | G5 | 6-FAM | VIC | NED | PET | LIZ | 100 | 135 | 41 | 16 | Nd |
| 15 | 310 | G5 | 6-FAM | VIC | TAMRA | PET | LIZ | 100 | 135 | 51 | 14 | Nd |
| 16 | 310 | G5 | 6-FAM | VIC | TAMRA | DY-510XL | DY-632 | 100 | 135 | 50 | 31 | 6 |
| 17 | 310 | G5 | 6-FAM | JOE | NED | PET | LIZ | 100 | 54 | 42 | 14 | Nd |
| 18 | 310 | G5 | 6-FAM | JOE | TAMRA | PET | LIZ | 100 | 54 | 52 | 14 | Nd |
| 19 | 310 | G5 | 6-FAM | JOE | ATTO550 | DY-510XL | DY-632 | 100 | 54 | 131 | 32 | 6 |
| 20 | 310 | G5 | 6-FAM | HEX | NED | PET | LIZ | 100 | 116 | 41 | 16 | Nd |
| 21 | 310 | G5 | 6-FAM | HEX | TAMRA | PET | LIZ | 100 | 104 | 51 | 14 | Nd |
| 22 | 310 | G5 | 6-FAM | HEX | TAMRA | DY-510XL | DY-632 | 100 | 104 | 50 | 31 | 6 |
| 23 | 310 | G5 | 6-FAM | HEX | ATTO 550 | DY-510XL | DY-632 | 100 | 115 | 103 | 40 | 7 |
| 24 | 310 | G5 | 6-FAM | HEX | ATTO 550 | ATTO 565 | DY-632 | 100 | 115 | 102 | 49 | 7 |
| 25 | 310 | G5 | 6-FAM | HEX | DY-548 | DY-510XL | DY-632 | 100 | 116 | 33 | 40 | 7 |
| 26 | 310 | G5 | 6-FAM | DY-530 | TAMRA | PET | LIZ | 100 | 148 | 51 | 14 | Nd |
| 27 | 310 | G5 | 6-FAM | DY-530 | TAMRA | DY-510XL | DY-632 | 100 | 148 | 51 | 31 | 6 |
| 28 | 310 | G5 | 6-FAM | DY-530 | ATTO 550 | DY-510XL | DY-632 | 100 | 126 | 103 | 41 | 7 |
| 29 | 310 | G5 | 6-FAM | DY-530 | ATTO 550 | ATTO 565 | DY-632 | 100 | 126 | 103 | 49 | 7 |
| 30 | 310 | G5 | 6-FAM | ATTO 532 | ATTO 550 | DY-510XL | DY-632 | 100 | 126 | 103 | 41 | 7 |
| 31 | 310 | G5 | 6-FAM | ATTO 532 | ATTO 550 | ATTO 565 | DY-632 | 100 | 126 | 103 | 49 | 7 |
| 32 | 310 | G5 | 6-FAM | CALFluor Orange 560 | ATTO 550 | DY-510XL | DY-632 | 100 | 136 | 103 | 40 | 7 |
| 33 | 3130 | Any4Dyes | 6-FAM | VIC | NED | ROX | — | 100 | 93 | 23 | 13 | — |
| 34 | 3130 | Any4Dyes | 6-FAM | DY-530 | ATTO 550 | ROX | — | 100 | 96 | 104 | 21 | — |
| 35 | 3130 | Any4Dyes | 6-FAM | HEX | ATTO 550 | ROX | — | 100 | 121 | 102 | 15 | — |
| 36 | 3130 | Any4Dyes | 6-FAM | HEX | DY-556 | ROX | — | 100 | 122 | 40 | 23 | — |
| 37 | 3130 | G5 | 6-FAM | VIC | NED | PET | LIZ | 100 | 91 | 67 | 39 | Nd |
| 38 | 3130 | Any5Dyes | 6-FAM | VIC | NED | PET | LIZ | 100 | 95 | 23 | 10 | Nd |
| 39 | 3130 | Any5Dyes | 6-FAM | HEX | ATTO 550 | DY-510XL | DY-632 | 100 | 83 | 83 | 32 | 7 |
| 40 | 3130 | Any5Dyes | 6-FAM | HEX | ATTO 550 | ATTO 565 | DY-632 | 100 | 87 | 85 | 39 | 7 |
| 41 | 3130 | Any5Dyes | 6-FAM | DY-530 | ATTO 550 | DY-510XL | DY-632 | 100 | 94 | 100 | 52 | 9.6 |
| 42 | 3130 | Any5Dyes | 6-FAM | DY-530 | ATTO 550 | DY-510XL | DY-520XL | 100 | 104 | 100 | 33 | 6.6 |
| 43 | 3130 | Any5Dyes | 6-FAM | DY-530 | ATTO 550 | ATTO 565 | DY-632 | 100 | 101 | 96 | 35 | 9.6 |
| 44 | 3130 | Any5Dyes | 6-FAM | DY-530 | ATTO 550 | ATTO 565 | DY-520XL | 100 | 100 | 102 | 38 | 4 | nd: not determined.

many) according to the instructions of the manufacturer. DNA quantification was done by UV/VIS spectroscopy (Sambrook et al., 1989) recording the absorbancy of nucleotide bases at 260 nm or quantitative real time PCR (qPCR) using the Quantifyler™ Human DNA quantification kit (Applied Biosystems, Foster City, Calif., USA) and an ABI Prism 7000 SDS real time thermocycler (Applied Biosystems, Foster City, Calif., USA).

The human STR-loci vWA (GenBank accession No. M25858), D12S391 (GenBank accession No. G08921), D18S51 (GenBank accession No. L18333) and D19S433 (GenBank accession No. G08036) were chosen. The *Homo sapiens* DNA database RefSeq Build 35 at NCBI (National Center for Biotechnology Information, Bethesda, Md., USA) was used for primer design. PCR primer design was done with the software Primer3 (Rozen S, Skaletsky H J. Primer3 on the www for general users and for biologist programmers. In: Krawetz S, Misener S (eds) Bioinformatics Methods and Protocols: Methods in Molecular Biology. Humana Press, Totowa, N.J., pp 365-386, 2000). The specificity of the primers was checked against the human genome sequence using the software Blastn (Basic Local Alignment Search Tool nucleotides; Altschul S F, Gish W, Miller W, Myers E W, Lipman D J. Basic local alignment search tool. J Mol Biol, Vol 215, pp 403-410, 1990). The compatibility of the primers pairs for multiplexing was controlled with the software Autodimer (Vallone P M, Butler J M. AutoDimer: a screening tool for primer-dimer and hairpin structures. Biotechniques, Vol 37, pp 226-231, 2004). Primers were synthesized and purified as outlined in example 1.

PCR setup was as described in example 2 with the following modifications: The oligonucleotide primers used and their final concentration within the PCR are shown in table 5, and 500 pg genomic human DNA was applied as template DNA per reaction.

TABLE 5

Evaluation of new fluorescence dye combinations for ABI Prism ® Genetic Analyzers.

| Primer name | DNA sequence (5'→3') | 5'-Dye | Concentration within PCR [nM] |
|---|---|---|---|
| vWA-F | TTTGCCCTTATTATTTTGTGAACTC | None | 300 |
| vWA-R | AGGACAGATGATAAATACATAGGATGG | 6-FAM | 300 |
| D12S391-F | AGTAGTTTCTTCTGGTGAAGGAAGA | ATTO 550 | 100 |
| D12S391-R | CTCCATATCACTTGAGCTAATTCCT | None | 100 |
| D18S51-F | CGACTACCAGCAACAACACAA | None | 400 |
| D18S51-R | ACTCTGAGTGACAAATTGAGACCTT | DY-510XL | 400 |
| D19S433-F | GCATGTTGGCACATTCCTGTA | DY-530 | 100 |
| D19S433-R | TGCACCCATTACCCGAATAAA | None | 100 | nd: not determined.

Figure 4:
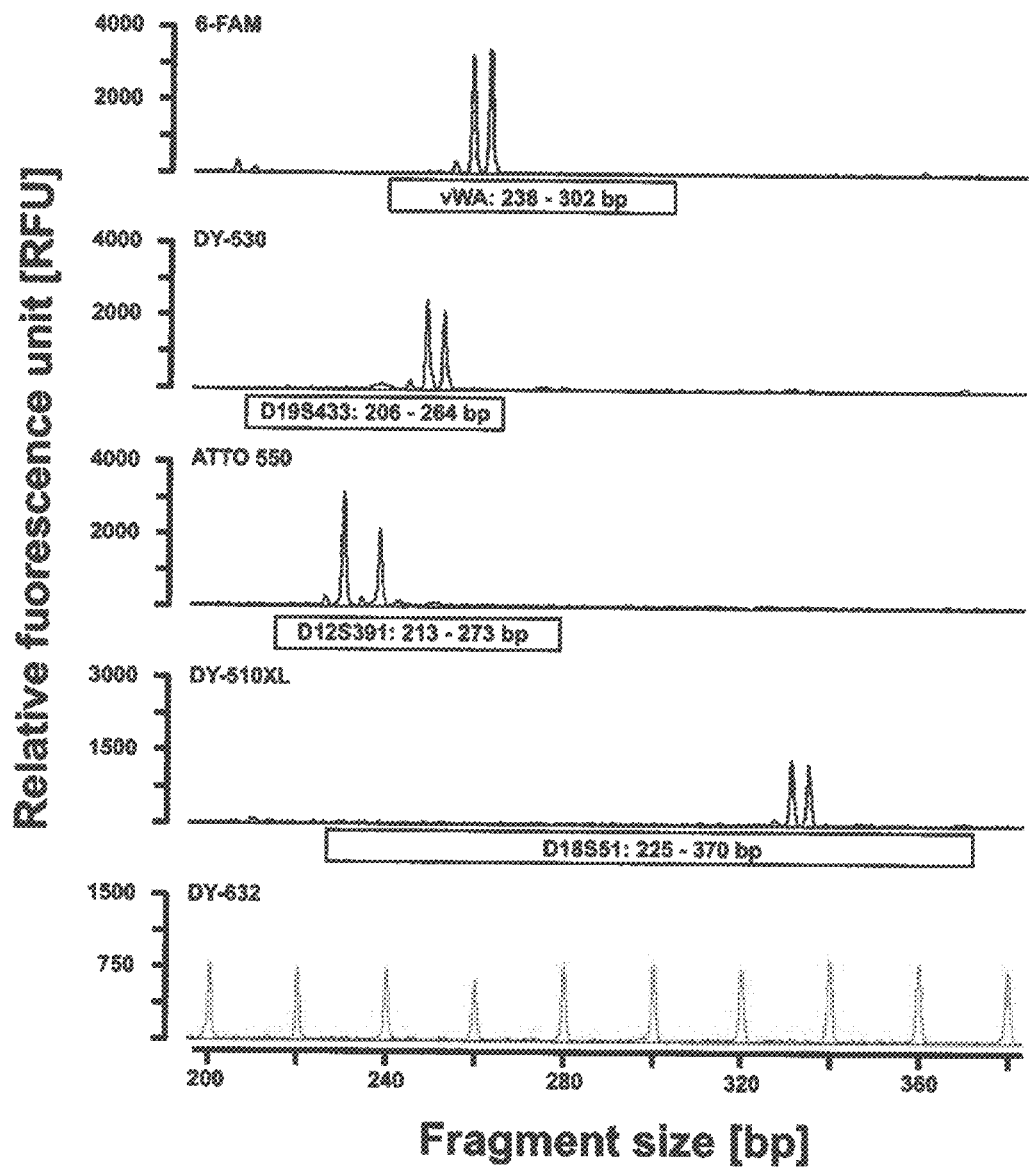
FIG. 4: Human DNA profiling by multiplex PCR amplification and genotyping of four short tandem repeats (STRs) with overlapping fragment ranges Electropherograms which show the relative fluorescent units (RFUs) for the dyes 6-FAM, DY-530, ATTO 550, DY-510-XL and DY-632 over the fragment size in basepairs [bp] are depicted. The multiplex PCR and genotyping was done as explained in the text for example 4 starting from 500 pg genomic DNA. An internal DY-632-labelled size standard was used to calculate the fragment size (electropherogram at bottom). The name of the STR locus and its fragment range is marked by a bare at the bottom of each electropherogram.
Figure 5:
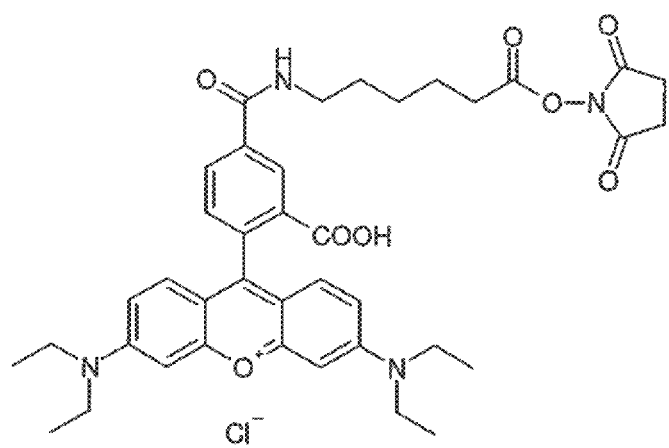
FIG. 5: Structures of fluorescence dye DY-555 (Dyomics GmbH (Jena, Germany)). Structure of NHS-ester of DY-555, chloride salt.

Aliquotes of 1 μL of the purified PCR products were withdrawn and mixed with 12.0 μL HiDi™ formamide (Applied Biosystems) and 0.5 L of DY-632 labelled length standard. The length standard was synthesized as described in example 2 and diluted in TE-buffer to give signal heights of approximately 700-1000 RFU/0.5 μL. Sample denaturation and capillary electrophoresis was done as outlined in example 3 using an ABI Prism® 310 Genetic Analyzer and the virtual filterset G5. The data were analyzed with the software GeneMapper®. A pre-run dye matrix file for the dye combination 6-FAM, DY-530, ATTO 550, DY-510XL and DY-632 for the filterset G5 was applied. Electropherograms showing the results for genomic DNA which was heterozygous in all four STR-loci are depicted in FIG. 4. As illustrated the five dyes could be clearly separated without spectral overlap. The amplicons gave sharp fragment peaks and the size calling with the self-made internal length standard was accurate and reproducible.

The following exemplary PCR primers have been used in the appended illustrative examples:

TABLE 6

List of PCR primers used in the examples with their respective SEQ ID NOs

| Sequence | Primer | Sequence | Primer |
|---|---|---|---|
| SEQ ID NO: 1 | PCR primer WB60 | SEQ ID NO: 15 | PCR primer WB320 |
| SEQ ID NO: 2 | PCR primer WB80 | SEQ ID NO: 16 | PCR primer WB340 |
| SEQ ID NO: 3 | PCR primer WB94 | SEQ ID NO: 17 | PCR primer WB360 |
| SEQ ID NO: 4 | PCR primer WB100 | SEQ ID NO: 18 | PCR primer WB380 |
| SEQ ID NO: 5 | PCR primer WB120 | SEQ ID NO: 19 | PCR primer Alpha3 |
| SEQ ID NO: 6 | PCR primer WB140 | SEQ ID NO: 20 | PCR primer vWA-F |
| SEQ ID NO: 7 | PCR primer WB160 | SEQ ID NO: 21 | PCR primer vWA-R |
| SEQ ID NO: 8 | PCR primer WB180 | SEQ ID NO: 22 | PCR primer D12S391-F |
| SEQ ID NO: 9 | PCR primer WB200 | SEQ ID NO: 23 | PCR primer D12S391-R |
| SEQ ID NO: 10 | PCR primer WB220 | SEQ ID NO: 24 | PCR primer D18S51-F |

TABLE 6-continued

List of PCR primers used in the examples with their respective SEQ ID NOs

| Sequence | Primer | Sequence | Primer |
|---|---|---|---|
| SEQ ID NO: 11 | PCR primer WB240 | SEQ ID NO: 25 | PCR primer D18S51-R |
| SEQ ID NO: 12 | PCR primer WB260 | SEQ ID NO: 26 | PCR primer D19S433-F |

TABLE 6-continued

List of PCR primers used in the examples with their respective SEQ ID NOs

| Sequence | Primer | Sequence | Primer |
| --- | --- | --- | --- |
| SEQ ID NO: 13 | PCR primer WB280 | SEQ ID NO: 27 | PCR primer D19S433-R |
| SEQ ID NO: 14 | PCR primer WB300 | | |

The invention claimed is:

1. A method for the simultaneous detection of at least four nucleic acids in a sample, each nucleic acid labelled with a covalently attached fluorescent dye, the method comprising detecting the fluorescence emission of each of the fluorescent dyes upon excitation, wherein
   (i) a first fluorescent dye selected from the group consisting of 5-FAM and 6-FAM or a blend thereof is covalently attached to a first nucleic acid,
   (ii) a second fluorescent dye selected from the group consisting of DY-530, HEX, CAL Fluor Orange 560 and ATTO 532 is covalently attached to a second nucleic acid,
   (iii) a third fluorescent dye selected from the group consisting of ATTO 550, DY-555 and DY-556 covalently attached to a third nucleic acid, and
   (iv) a fourth fluorescent dye selected from the group consisting of ROX, DY-510 XL, and ATTO 565 is covalently attached to a fourth nucleic acid, and
   (v) optionally a fifth fluorescent dye selected from the group consisting of DY-632 and DY-520 XL is covalently attached to a fifth nucleic acid.

2. The method of claim 1 further comprising simultaneous detection of fluorescently labelled amplification products from a nucleic acid amplification reaction, comprising the steps of
   (a) amplifying four or more nucleic acid sequences using primers or pairs of primers flanking the nucleic acid sequences to he amplified; and
   (b) detecting either the fluorescently labelled amplification products directly or indirectly using fluorescently labelled oligonucleotide probes complementary to said amplification products and
   (c) optionally detecting a fluorescently labelled size marker,
wherein for each nucleic acid sequence to be detected a fluorescent dye is covalently attached to said fluorescently labelled amplification product and/or to said oligonucleotide probe and/or to said primer and/or to at least one primer of said primer pair and optionally to a size marker.

3. The method according to claim 2, wherein the nucleic acid amplification reaction is selected from the group consisting of polymerase chain reaction (PCR), ligase chain reaction (LCR), transcription-based amplification system (TAS), nucleic acid sequence based amplification (NASBA), rolling circle amplification (RCA), transcription-mediated amplification (TMA), self-sustaining sequence replication (3SR), Qβamplification and (thermostable) helicase dependent amplification ((t)HAD).

4. The method according to claim 2, wherein said nucleic acid sequences are amplified simultaneously.

5. The method according to claim 2, wherein the nucleic acid amplification reaction is a multiplex PCR.

6. The method according to claim 2, additionally comprising separating the fluorescently labelled amplification products by their size or molecular weight before detecting said fluorescentiy labelled amplification products.

7. The method according to claim 2, wherein the amplification reaction is real-time multiplex polymerase chain reaction and the method comprises
   (i) simultaneously amplifying at least four nucleic acid sequences using pairs of primers flanking said sequences to be amplified;
   (ii) detecting said amplification products using at least one oligonucleotide probe for each sequence to be amplified, wherein said oligonucleotide probe is substantially complementary to a sequence on said amplification product,
   wherein the first through fourth fluorescent dyes are covalently attached to separate oligonucleotide probes.

8. The method according to claim 2, wherein at least one nucleic acid is an oligonucleotide size marker.

9. A composition comprising;
   (i) a first nucleic acid to which a fluorescent dye selected from the group consisting of 5-FAM and 6-FAM or a blend thereof is covalently attached;
   (ii) a second nucleic acid to which a fluorescent dye selected from the group consisting of DY-530, HEX, CAL Fluor Orange 560 and ATTO 532 is covalently attached;
   (iii) a third nucleic acid to which a fluorescent dye selected from the group consisting of ATTO 550, DY-555 and DY-556 is covalently attached, and
   (iv) a fourth nucleic acid to which a fluorescent dye selected from the group consisting of ROX, DY-510XL, and ATTO 565 is covalently attached.

10. The composition according to claim 9, additionally comprising:
   (v) a fifth nucleic acid to which a fluorescent dye selected from the group consisting of DY-632 and DY-520XL is covalently attached.

11. The composition according to claim 9, wherein at least one nucleic acid is an oligonucleotide size marker.

12. The composition according to claim 9, wherein each nucleic acid is a member of a same allelic ladder.

13. A kit for multiplex PCR comprising
   (i) at least one first nucleic acid to which a first fluorescent dye selected from the group consisting of 5-FAM and 6-FAM or a blend thereof is covalently attached;
   (ii) at least one second nucleic to which a second fluorescent dye selected from the group consisting of DY-530, HEX, CAL Fluor Orange 560 and ATTO 532 is covalently attached;
   (iii) at least one third nucleic acid to which a third fluorescent dye selected from the group consisting of ATTO 550, DY-555 and DY-556 is covalently attached, and
   (iv) at least one fourth nucleic acid to which a fourth fluorescent dye selected from the group consisting of ROX, DY-510 OXL, and ATTO 565 is covalently attached.

14. The kit according to claim 13, wherein the first, second, third and/or fourth nucleic acid is a probe or a primer.

15. The kit for multiplex PCR according to claim 13 comprising:
   (i) at least three different pairs of primers, wherein to at least one primer of each pair a primer fluorescent dye is covalently attached; and
   (ii) optionally an oligonucleotide size marker, wherein a fluorescent dye is covalently attached to said size marker;
wherein the primer fluorescent dyes comprise at least four different fluorescent dyes wherein a first dye is 5-FAM or 6-FAM or a blend thereof, a second dye is selected from the group of DY-530, HEX, CAL Fluor Orange 560 and ATTO 532, a third dye is selected from the group consisting of ATTO 550, DY-555 and DY-556, a fourth dye is selected from the group consisting of ROX, DY-510XL and ATTO 565 and optionally a fifth fluorescent dye is selected from the group consisting of DY-632 and DY-520XL.

16. The kit according to claim 13 comprising at least five different fluorescent dyes, wherein the third dye is ATTO 550 and the fourth dye is selected from the group consisting of DY-510XL and ATTO 565.

17. A method of conducting a multiplex polymerase chain reaction comprising at least four fluorescent dyes, wherein each dye is covalently attached to an oligonucleotide primer substantially complementary to a sequence flanking a locus to he amplified or to an oligonucleotide probe substantially complementary to a sequence on the locus to be amplified and wherein
   (i) a first dye is 5-FAM or 6-FAM or a blend thereof,
   (ii) a second dye is selected from the group consisting of DY-530, HEX, CAL Fluor Orange 560 and ATTO 532,
   (iii) a third dye is selected from the group consisting of ATTO 550 and DY-555, DY-556,
   (iv) a fourth dye is selected from the group consisting of ROX, DY-510XL, and ATTO 565, and consisting of DY-632 and DY-520XL and optionally a fifth dye is selected from the group consisting of DY-632 and DY-520XL.

* * * * *